(12) United States Patent
Davenport et al.

(10) Patent No.: US 8,956,361 B2
(45) Date of Patent: *Feb. 17, 2015

(54) EXTENDED TAB BONE SCREW SYSTEM

(71) Applicant: Amendia, Inc., Marietta, GA (US)

(72) Inventors: Alan Davenport, Flowery Branch, GA (US); Jeffrey Radcliffe, Marietta, GA (US); Timothy Lusby, Marietta, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/720,525

(22) Filed: Dec. 19, 2012

(65) Prior Publication Data

US 2013/0172937 A1    Jul. 4, 2013

Related U.S. Application Data

(60) Provisional application No. 61/577,247, filed on Dec. 19, 2011.

(51) Int. Cl.
*A61B 17/88* (2006.01)
*A61B 17/70* (2006.01)
*A61B 19/00* (2006.01)

(52) U.S. Cl.
CPC ......... *A61B 17/7032* (2013.01); *A61B 17/7037* (2013.01); *A61B 17/7085* (2013.01); *A61B 17/7089* (2013.01); *A61B 2019/307* (2013.01); Y10S 606/914 (2013.01)
USPC .......................... 606/86 A; 606/104; 606/914

(58) Field of Classification Search
USPC ................ 606/86 A, 104, 914, 916, 266–270
See application file for complete search history.

(56) References Cited

U.S. PATENT DOCUMENTS

| | | |
|---|---|---|
| 5,545,180 A | 8/1996 | Le et al. |
| 5,653,710 A | 8/1997 | Harle |
| 5,716,355 A | 2/1998 | Jackson et al. |
| 5,720,751 A | 2/1998 | Jackson |
| 5,725,541 A | 3/1998 | Anspach, III et al. |
| 5,741,282 A | 4/1998 | Anspach, III et al. |
| 5,782,833 A * | 7/1998 | Haider .......................... 606/266 |
| 5,797,911 A | 8/1998 | Sherman et al. |
| 5,879,350 A | 3/1999 | Sherman et al. |
| 5,885,286 A | 3/1999 | Sherman et al. |
| 5,928,244 A | 7/1999 | Tovey et al. |
| 5,941,885 A | 8/1999 | Jackson |
| 5,957,435 A | 9/1999 | Bronstad |
| 6,004,349 A | 12/1999 | Jackson |
| 6,053,917 A | 4/2000 | Sherman et al. |
| 6,056,753 A | 5/2000 | Jackson |
| 6,102,913 A | 8/2000 | Jackson |
| 6,110,172 A | 8/2000 | Jackson |
| 6,179,841 B1 | 1/2001 | Jackson |
| 6,193,719 B1 | 2/2001 | Gournay et al. |
| 6,224,596 B1 | 5/2001 | Jackson |
| 6,224,598 B1 | 5/2001 | Jackson |
| 6,251,112 B1 | 6/2001 | Jackson |
| 6,258,090 B1 | 7/2001 | Jackson |
| 6,261,288 B1 | 7/2001 | Jackson |

(Continued)

*Primary Examiner* — Jerry Cumberledge
(74) *Attorney, Agent, or Firm* — David L King

(57) ABSTRACT

A bone screw system is presented. The bone screw system has a fixation element, a receiving element, coupling element, and a compression element. In one aspect, the system also has a pair of leg extensions extending upwardly therefrom the receiving element.

7 Claims, 16 Drawing Sheets

(56) References Cited

U.S. PATENT DOCUMENTS

| | | |
|---|---|---|
| 6,280,445 B1 | 8/2001 | Morrison et al. |
| 6,296,642 B1 | 10/2001 | Morrison et al. |
| 6,361,535 B2 | 3/2002 | Jackson |
| 6,368,321 B1 | 4/2002 | Jackson |
| 6,379,356 B1 | 4/2002 | Jackson |
| 6,440,132 B1 | 8/2002 | Jackson |
| 6,454,768 B1 | 9/2002 | Jackson |
| 6,454,772 B1 | 9/2002 | Jackson |
| 6,478,795 B1 | 11/2002 | Gournay et al. |
| 6,565,567 B1 * | 5/2003 | Haider ............... 606/266 |
| 6,699,248 B2 | 3/2004 | Jackson |
| 6,716,214 B1 | 4/2004 | Jackson |
| 6,723,099 B1 | 4/2004 | Goshert |
| 6,726,687 B2 | 4/2004 | Jackson |
| 6,726,689 B2 | 4/2004 | Jackson |
| 6,730,089 B2 | 5/2004 | Jackson |
| 6,869,433 B2 * | 3/2005 | Glascott ............... 606/308 |
| 6,884,244 B1 | 4/2005 | Jackson |
| 6,964,666 B2 | 11/2005 | Jackson |
| 6,997,927 B2 | 2/2006 | Jackson |
| 7,033,174 B2 | 4/2006 | Giorno |
| 7,037,324 B2 | 5/2006 | Martinek |
| 7,141,051 B2 * | 11/2006 | Janowski et al. ........ 606/272 |
| 7,160,300 B2 * | 1/2007 | Jackson ............... 606/273 |
| 7,204,838 B2 | 4/2007 | Jackson |
| 7,217,130 B2 | 5/2007 | Giorno |
| 7,235,100 B2 | 6/2007 | Martinek |
| 7,270,665 B2 | 9/2007 | Morrison et al. |
| 7,309,346 B2 | 12/2007 | Martinek |
| 7,322,981 B2 | 1/2008 | Jackson |
| 7,335,202 B2 * | 2/2008 | Matthis et al. ........ 606/266 |
| 7,465,306 B2 * | 12/2008 | Pond et al. ............ 606/86 A |
| 7,470,279 B2 | 12/2008 | Jackson |
| 7,476,239 B2 | 1/2009 | Jackson |
| 7,513,905 B2 | 4/2009 | Jackson |
| 7,563,281 B2 | 7/2009 | Sears et al. |
| 7,572,279 B2 | 8/2009 | Jackson |
| 7,575,576 B2 * | 8/2009 | Zubok et al. ............ 606/90 |
| 7,597,694 B2 | 10/2009 | Lim et al. |
| 7,621,918 B2 | 11/2009 | Jackson |
| 7,625,396 B2 | 12/2009 | Jackson |
| 7,641,674 B2 | 1/2010 | Young |
| 7,651,502 B2 | 1/2010 | Jackson |
| 7,662,175 B2 | 2/2010 | Jackson |
| 7,670,142 B2 | 3/2010 | Giorno |
| 7,722,623 B2 | 5/2010 | Franks et al. |
| 7,749,233 B2 * | 7/2010 | Farr et al. ............... 606/104 |
| 7,766,915 B2 | 8/2010 | Jackson |
| 7,776,067 B2 | 8/2010 | Jackson |
| 7,789,896 B2 | 9/2010 | Jackson |
| 7,833,250 B2 | 11/2010 | Jackson |
| 7,837,710 B2 | 11/2010 | Lombardo et al. |
| 7,837,714 B2 | 11/2010 | Drewry et al. |
| 7,837,716 B2 | 11/2010 | Jackson |
| 7,846,187 B2 | 12/2010 | Jackson |
| 7,901,437 B2 | 3/2011 | Jackson |
| 7,905,907 B2 * | 3/2011 | Spitler et al. ............ 606/279 |
| 7,914,559 B2 | 3/2011 | Carls et al. |
| 7,927,360 B2 | 4/2011 | Pond, Jr. et al. |
| 7,946,657 B2 | 5/2011 | Hall et al. |
| 7,951,170 B2 | 5/2011 | Jackson |
| 7,967,821 B2 | 6/2011 | Sicvol et al. |
| 7,967,850 B2 | 6/2011 | Jackson |
| 8,002,804 B2 | 8/2011 | Lim et al. |
| 8,012,213 B2 | 9/2011 | Sears et al. |
| 8,028,608 B2 | 10/2011 | Sixto, Jr. et al. |
| 8,034,087 B2 | 10/2011 | Jackson |
| 8,052,720 B2 | 11/2011 | Kuester et al. |
| 8,052,724 B2 | 11/2011 | Jackson |
| 8,062,295 B2 | 11/2011 | McDevitt et al. |
| 8,066,739 B2 | 11/2011 | Jackson |
| 8,066,744 B2 | 11/2011 | Justis et al. |
| 8,092,500 B2 | 1/2012 | Jackson |
| 8,092,502 B2 | 1/2012 | Jackson |
| 8,100,909 B2 | 1/2012 | Butler et al. |
| 8,100,915 B2 * | 1/2012 | Jackson ............... 606/86 A |
| 8,105,328 B2 | 1/2012 | Protopsaltis |
| 8,123,751 B2 | 2/2012 | Shluzas |
| 8,128,667 B2 | 3/2012 | Jackson |
| 8,137,386 B2 | 3/2012 | Jackson |
| 8,142,483 B2 | 3/2012 | Drewry et al. |
| 8,162,948 B2 | 4/2012 | Jackson |
| 8,202,302 B2 | 6/2012 | Perez-Cruet et al. |
| 8,211,151 B2 | 7/2012 | Schwab et al. |
| 8,221,478 B2 | 7/2012 | Patterson et al. |
| 8,241,333 B2 | 8/2012 | Jackson |
| 8,246,665 B2 | 8/2012 | Butler et al. |
| 8,257,396 B2 | 9/2012 | Jackson |
| 8,257,398 B2 | 9/2012 | Jackson |
| 8,257,402 B2 | 9/2012 | Jackson |
| 8,262,662 B2 | 9/2012 | Beardsley et al. |
| 8,273,089 B2 | 9/2012 | Jackson |
| 8,273,109 B2 | 9/2012 | Jackson |
| 8,292,892 B2 | 10/2012 | Jackson |
| 8,292,926 B2 | 10/2012 | Jackson |
| 8,303,628 B2 | 11/2012 | Dewey et al. |
| 8,308,782 B2 | 11/2012 | Jackson |
| 8,317,443 B2 | 11/2012 | Stauch et al. |
| 8,333,770 B2 | 12/2012 | Hua |
| 8,469,960 B2 * | 6/2013 | Hutton et al. ............ 606/86 A |
| 8,747,407 B2 * | 6/2014 | Gorek ............... 606/86 A |
| 2002/0133159 A1 | 9/2002 | Jackson |
| 2003/0125741 A1 * | 7/2003 | Biedermann et al. ....... 606/61 |
| 2004/0167525 A1 | 8/2004 | Jackson |
| 2004/0215190 A1 * | 10/2004 | Nguyen et al. ............ 606/61 |
| 2005/0021033 A1 | 1/2005 | Zeiler et al. |
| 2005/0182410 A1 | 8/2005 | Jackson |
| 2005/0187549 A1 | 8/2005 | Jackson |
| 2005/0267477 A1 | 12/2005 | Jackson |
| 2006/0009773 A1 | 1/2006 | Jackson |
| 2006/0025771 A1 | 2/2006 | Jackson |
| 2006/0058794 A1 | 3/2006 | Jackson |
| 2006/0064089 A1 | 3/2006 | Jackson |
| 2006/0069391 A1 | 3/2006 | Jackson |
| 2006/0079892 A1 | 4/2006 | Roychowdhury et al. |
| 2006/0083603 A1 | 4/2006 | Jackson |
| 2006/0084979 A1 | 4/2006 | Jackson |
| 2006/0184178 A1 | 8/2006 | Jackson |
| 2006/0200136 A1 | 9/2006 | Jackson |
| 2006/0241602 A1 | 10/2006 | Jackson |
| 2006/0241603 A1 | 10/2006 | Jackson |
| 2006/0293680 A1 | 12/2006 | Jackson |
| 2006/0293693 A1 * | 12/2006 | Farr et al. ............... 606/104 |
| 2007/0016200 A1 | 1/2007 | Jackson |
| 2007/0233079 A1 * | 10/2007 | Fallin et al. ............ 606/61 |
| 2007/0288003 A1 | 12/2007 | Dewey et al. |
| 2008/0082103 A1 * | 4/2008 | Hutton et al. ............ 606/73 |
| 2008/0119849 A1 * | 5/2008 | Beardsley et al. .......... 606/61 |
| 2008/0125817 A1 * | 5/2008 | Arnett et al. ............ 606/319 |
| 2008/0140076 A1 | 6/2008 | Jackson |
| 2008/0140118 A1 | 6/2008 | Martinek |
| 2008/0147122 A1 | 6/2008 | Jackson |
| 2008/0154315 A1 | 6/2008 | Jackson |
| 2008/0300638 A1 | 12/2008 | Beardsley et al. |
| 2009/0036935 A1 | 2/2009 | Jackson |
| 2009/0048634 A1 | 2/2009 | Jackson |
| 2009/0062860 A1 | 3/2009 | Frasier et al. |
| 2009/0093844 A1 | 4/2009 | Jackson |
| 2009/0105762 A1 | 4/2009 | Jackson |
| 2009/0105764 A1 | 4/2009 | Jackson |
| 2009/0105820 A1 | 4/2009 | Jackson |
| 2009/0198290 A1 | 8/2009 | Armstrong et al. |
| 2009/0228052 A1 | 9/2009 | Beardsley et al. |
| 2009/0228055 A1 | 9/2009 | Jackson |
| 2009/0259259 A1 | 10/2009 | Jackson |
| 2009/0299414 A1 | 12/2009 | Jackson |
| 2009/0318972 A1 | 12/2009 | Jackson |
| 2010/0016904 A1 | 1/2010 | Jackson |
| 2010/0030280 A1 | 2/2010 | Jackson |
| 2010/0036433 A1 | 2/2010 | Jackson |
| 2010/0049206 A1 | 2/2010 | Biyani |
| 2010/0179573 A1 | 7/2010 | Levinsohn et al. |
| 2010/0191293 A1 | 7/2010 | Jackson |
| 2010/0198268 A1 | 8/2010 | Zhang et al. |

(56) References Cited

U.S. PATENT DOCUMENTS

| | | |
|---|---|---|
| 2010/0211114 A1 | 8/2010 | Jackson |
| 2010/0262195 A1 | 10/2010 | Jackson |
| 2010/0318136 A1 | 12/2010 | Jackson et al. |
| 2010/0331887 A1 | 12/2010 | Jackson et al. |
| 2011/0009910 A1 | 1/2011 | Jackson |
| 2011/0015678 A1 | 1/2011 | Jackson |
| 2011/0015683 A1 | 1/2011 | Jackson |
| 2011/0040335 A1 | 2/2011 | Stihl et al. |
| 2011/0040338 A1 | 2/2011 | Jackson |
| 2011/0066191 A1 | 3/2011 | Jackson |
| 2011/0098755 A1 | 4/2011 | Jackson et al. |
| 2011/0106176 A1 | 5/2011 | Jackson |
| 2011/0106179 A1 | 5/2011 | Prevost et al. |
| 2011/0137348 A1 | 6/2011 | Jackson |
| 2011/0137353 A1 | 6/2011 | Buttermann |
| 2011/0160775 A1 | 6/2011 | Carls et al. |
| 2011/0172715 A1 | 7/2011 | Pond, Jr. et al. |
| 2011/0178560 A1* | 7/2011 | Butler et al. ............... 606/86 A |
| 2011/0184469 A1 | 7/2011 | Ballard et al. |
| 2011/0208314 A1 | 8/2011 | Sears et al. |
| 2011/0218578 A1 | 9/2011 | Jackson |
| 2011/0218579 A1 | 9/2011 | Jackson |
| 2011/0245878 A1 | 10/2011 | Franks et al. |
| 2011/0282399 A1 | 11/2011 | Jackson |
| 2011/0306984 A1 | 12/2011 | Sasing |
| 2012/0029566 A1 | 2/2012 | Rezach |
| 2012/0029567 A1 | 2/2012 | Zolotov et al. |
| 2012/0035663 A1 | 2/2012 | Jackson |
| 2012/0035669 A1 | 2/2012 | Jackson |
| 2012/0035670 A1 | 2/2012 | Jackson et al. |
| 2012/0041484 A1 | 2/2012 | Briganti et al. |
| 2012/0041493 A1 | 2/2012 | Miller et al. |
| 2012/0046700 A1 | 2/2012 | Jackson et al. |
| 2012/0059426 A1 | 3/2012 | Jackson et al. |
| 2012/0071886 A1 | 3/2012 | Jackson |
| 2012/0089196 A1 | 4/2012 | Jackson |
| 2012/0095464 A9 | 4/2012 | Zeiler et al. |
| 2012/0095515 A1 | 4/2012 | Hamilton |
| 2012/0109220 A1 | 5/2012 | Jackson |
| 2012/0123477 A1 | 5/2012 | Landry et al. |
| 2012/0123483 A1 | 5/2012 | Perez-Cruet et al. |
| 2012/0143266 A1 | 6/2012 | Jackson et al. |
| 2012/0150232 A1 | 6/2012 | Van Nortwick et al. |
| 2012/0158070 A1 | 6/2012 | Jackson |
| 2012/0165873 A1 | 6/2012 | Perez-Cruet et al. |
| 2012/0179212 A1 | 7/2012 | Jackson et al. |
| 2012/0197309 A1 | 8/2012 | Steele |
| 2012/0209336 A1 | 8/2012 | Jackson et al. |
| 2012/0214127 A1 | 8/2012 | Drapeau et al. |
| 2012/0221054 A1 | 8/2012 | Jackson |
| 2012/0265257 A1 | 10/2012 | Jackson |
| 2012/0277800 A1 | 11/2012 | Jackson |
| 2012/0303070 A1 | 11/2012 | Jackson |
| 2012/0310286 A1 | 12/2012 | Jackson |
| 2012/0310290 A1 | 12/2012 | Jackson |
| 2012/0310291 A1 | 12/2012 | Jackson |
| 2012/0323279 A1 | 12/2012 | Tsuang et al. |
| 2014/0135854 A1* | 5/2014 | Dec et al. .................. 606/86 A |

* cited by examiner

EXTENDED TAB BONE SCREW SYSTEM

CONTINUITY

This application claims the benefit of U.S. Patent Application 61/577,247 entitled "Bone Screw System" filed on Dec. 19, 2011, which is incorporated herein in its entirety by reference.

FIELD OF THE INVENTION

Presented herein is a bone screw system. More specifically, a bone screw for use in spinal surgery is presented.

BACKGROUND OF THE INVENTION

Spinal surgeons often treat spinal disorders with spinal fusion augmented with elongated spinal rods connected to the spine with pedicle screws. Such "rod assemblies" generally comprise one or two spinal rods and a plurality of screws inserted through the pedicles and into their respective vertebral bodies. The screws are provided with connectors, for coupling the spinal rods to the screws. The spinal rods extend along the longitudinal axis of the spine, coupling to the plurality of screws via their connectors. The aligning influence of the rods forces the patient's spine to conform to a more appropriate shape.

SUMMARY

Presented herein is a bone screw system that comprises a fixation element, a receiving element, coupling element, and a compression element. The fixation element can be a screw. The receiving element defines an internal bore sized to receive the shank portion of the fixation element and a seat adapted to support the head portion of the fixation element. The seat of the receiving element is shaped to substantially conform to an exterior portion of the head portion of the fixation element.

The receiving element is further adapted to receive a stabilizer rod. As such, in one aspect, the receiving element comprises a pair of opposed legs separated by a rod-receiving channel. In another aspect, the bone screw system also comprises a pair of leg extensions. Each leg extension has a first end and a second end, where the second end is coupled to a respective opposed leg of the receiving element.

The compression element is engagable with the receiving element. In one aspect, the compression element is adapted to move downward into the compression element receiving chamber to translate a force to the stabilizer rod and translate a force onto the head portion of the fixation element and substantially fix the position of the fixation element with respect to the receiving element.

Other aspects and embodiments of the bone screw system are described herein. This description is meant to fully describe the bone screw system, but not limit its design, function, or application.

BRIEF DESCRIPTION OF THE DRAWINGS

These and other features of the preferred embodiments of the present invention will become more apparent in the detailed description in which reference is made to the appended drawings wherein.

DETAILED DESCRIPTION OF THE INVENTION

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an," and "the" include plural referents unless the context clearly dictates otherwise. Thus, for example, reference to "a screw" can include two or more such screws unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Figure 1:
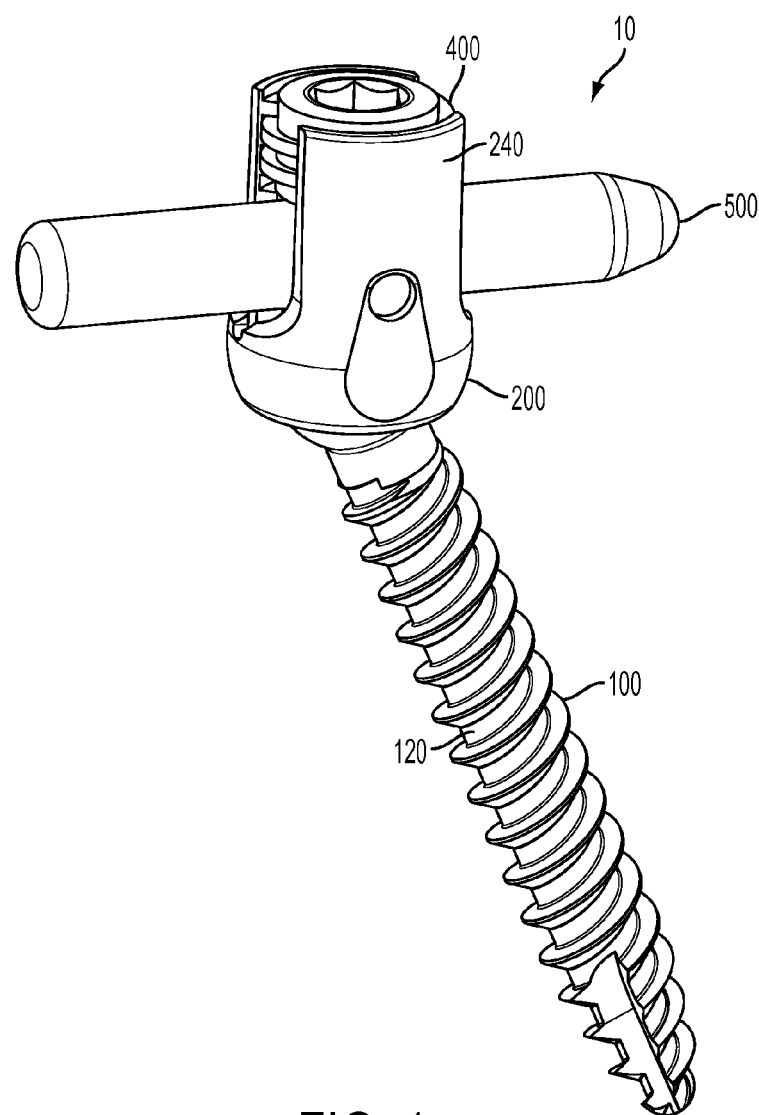
FIG. 1 is a perspective view of one aspect of a bone screw system.
Figure 2:
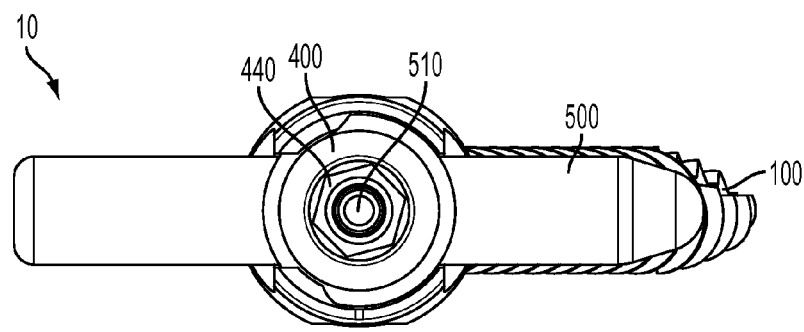
FIG. 2 is a top plan view of the bone screw system of FIG. 1, showing a portion of the stabilizer rod.
Figure 4:
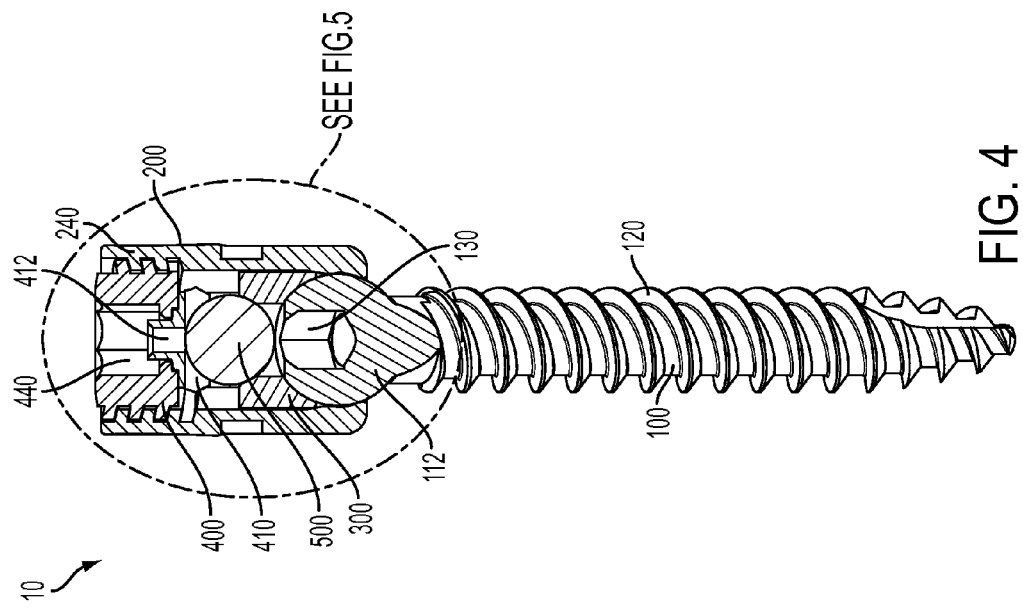
FIG. 4 is a cut-away right side elevation view of the bone screw system of FIG. 1, cut along line 4-4 of FIG. 3.
Figure 3:
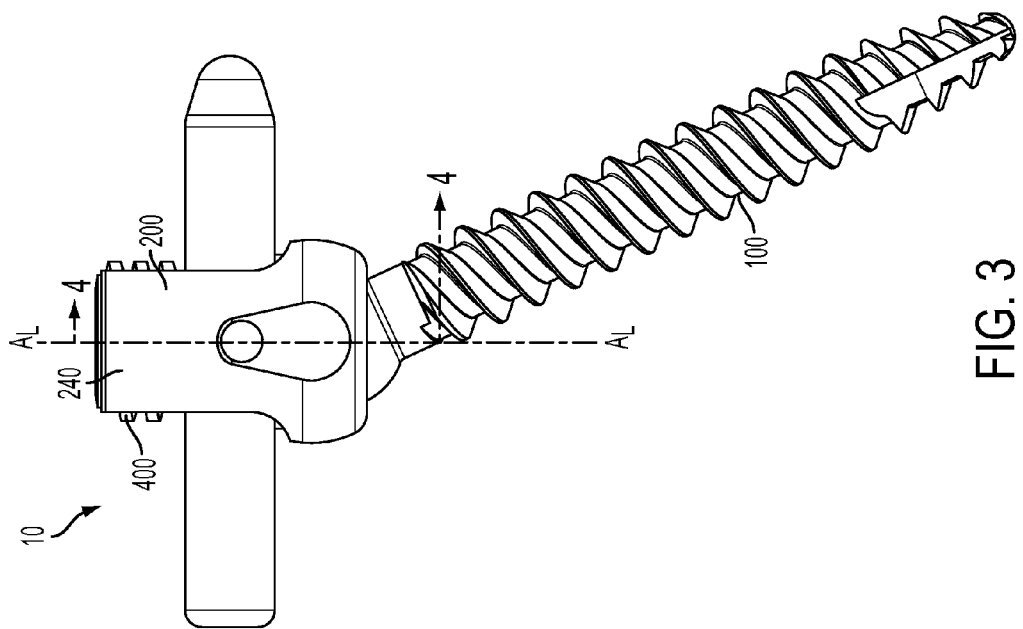
FIG. 3 is a front elevational view of the bone screw system of FIG. 1.
Figure 5:
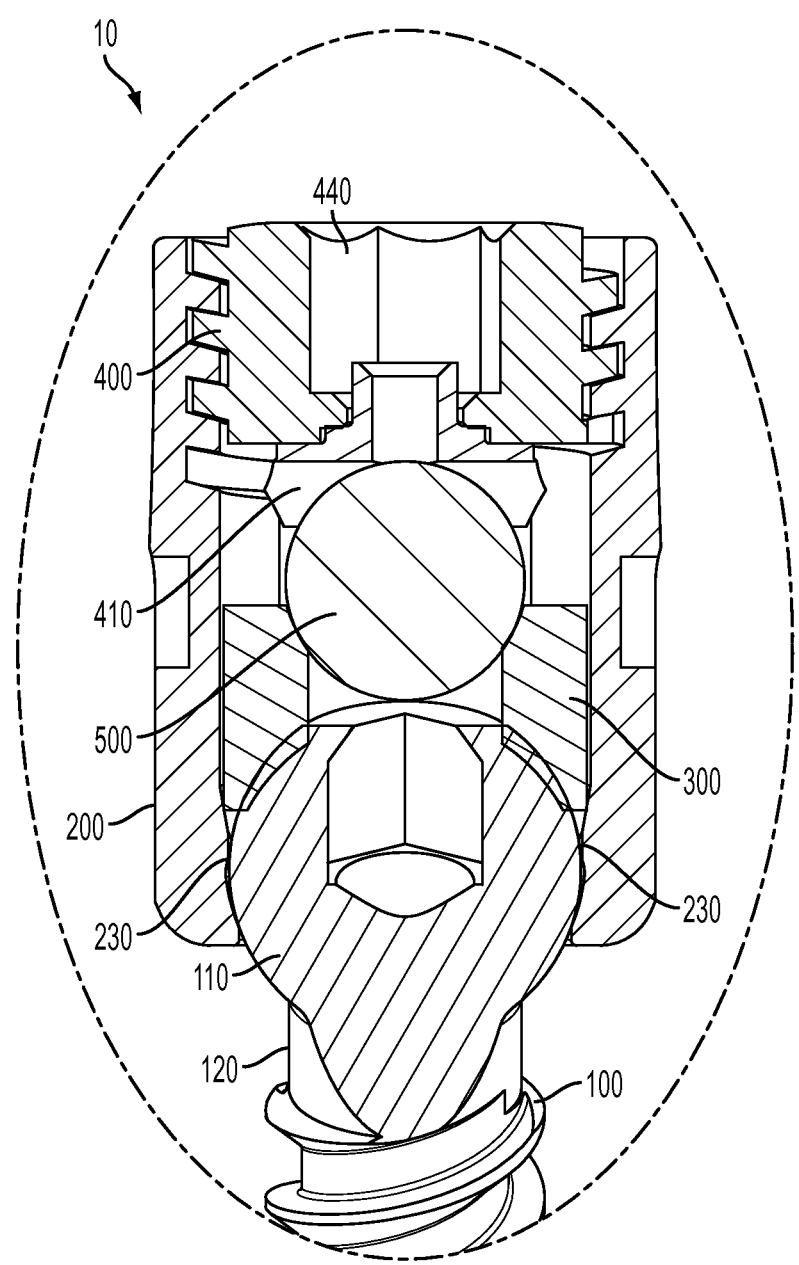
FIG. 5 is an exploded cut-away front elevational view of Section 5 of FIG. 4 of the bone screw system of FIG. 1
Figures 6, 7:
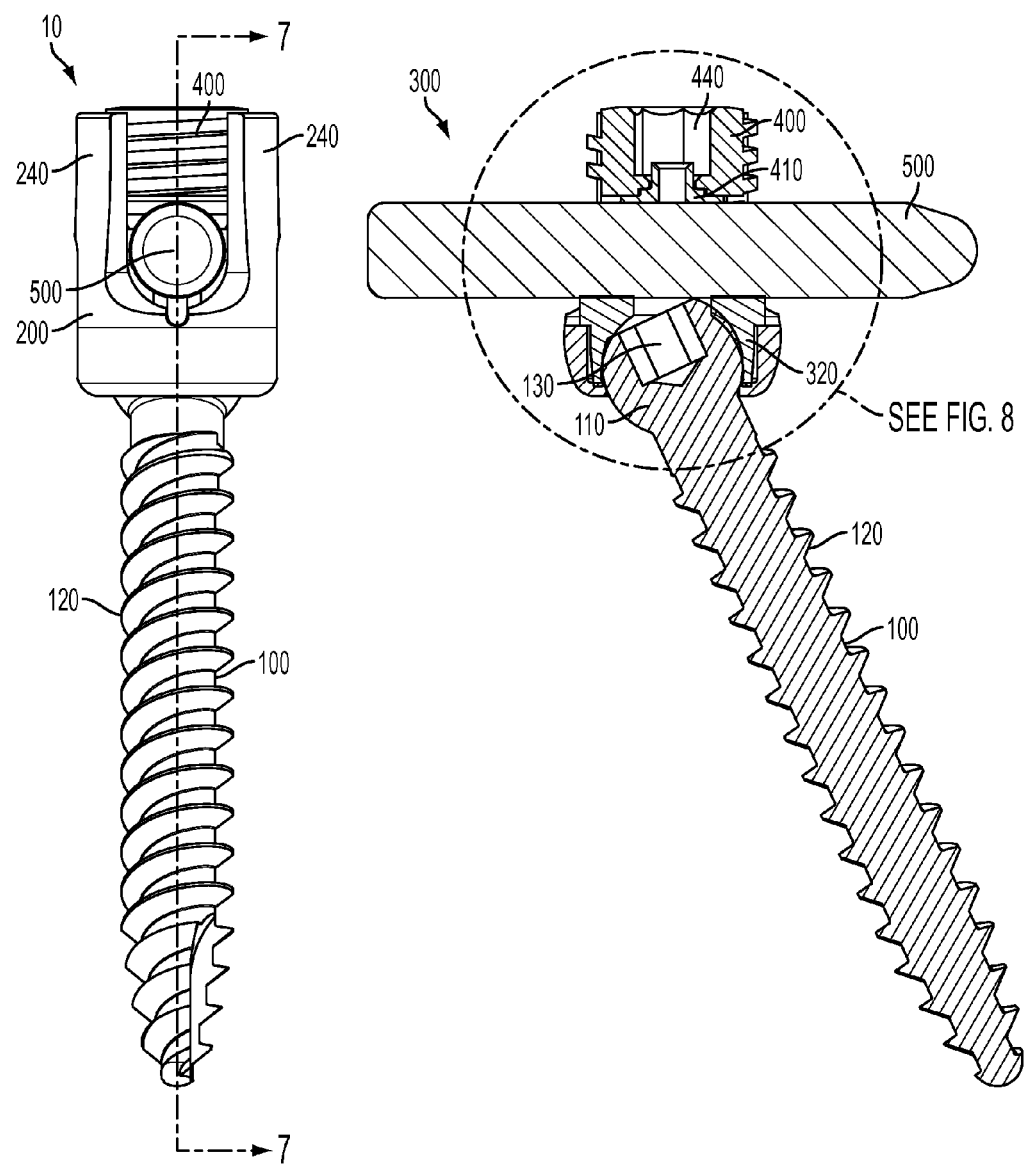
FIG. 6 is a right side elevational view of the bone screw system of FIG. 1.
FIG. 7 a cut-away front elevational view of the bone screw system of FIG. 1, cut along line 7-7 of FIG. 6.
Figure 8:
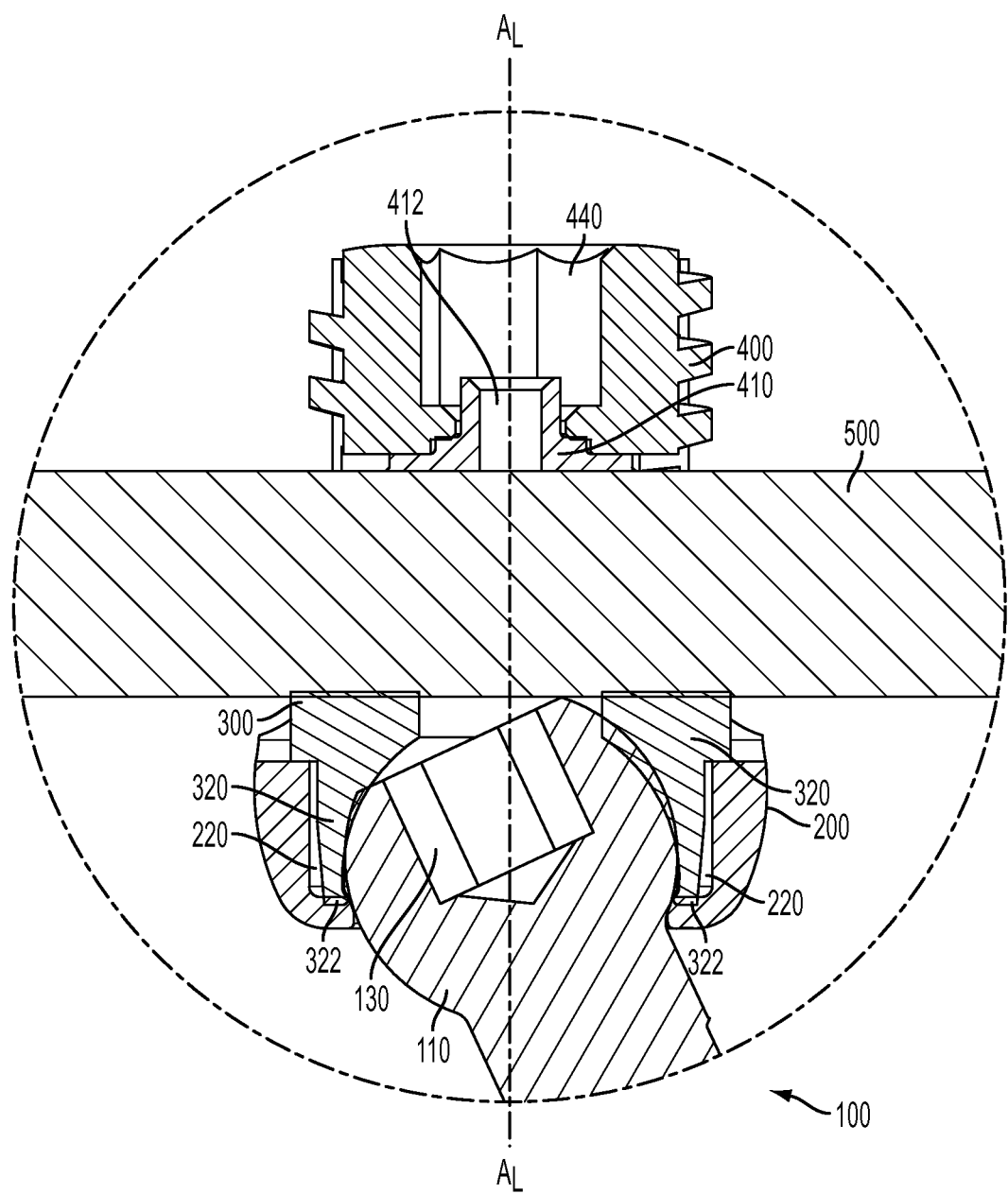
FIG. 8 is an exploded cut-away front elevational view of Section 8 of FIG. 7 of the bone screw system of FIG. 1.
Figure 9:
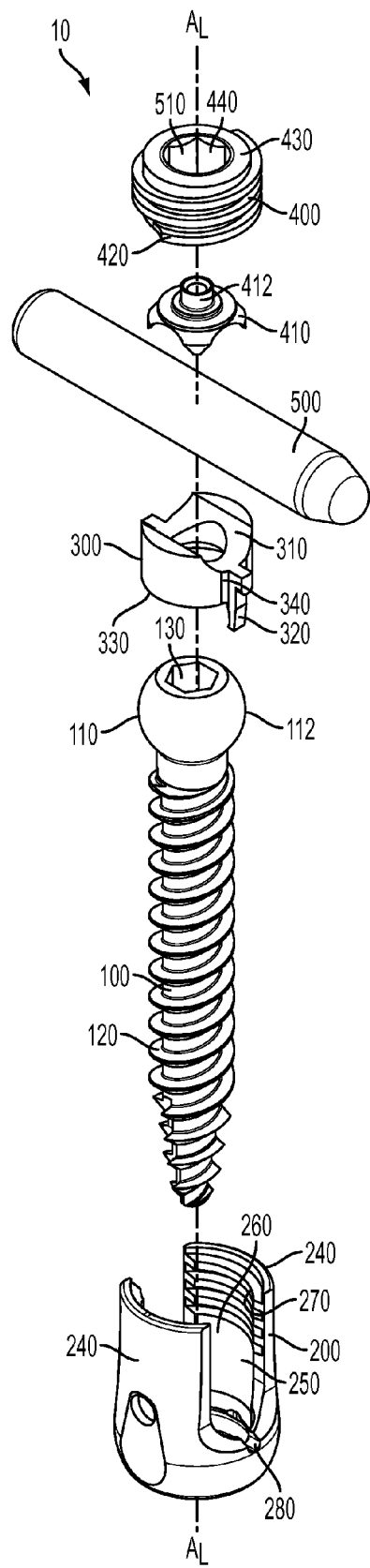
FIG. 9 is an exploded front perspective view of the bone screw system of FIG. 1.

Presented herein is a bone screw system 10 that comprises a fixation element 100, a receiving element 200, coupling element 300, and a compression element 400. In one aspect, the fixation element 100 is adapted to engage a bone and has a head portion 110 and a threaded shank portion 120. The fixation element can be a screw. In an exemplified aspect, the head portion is substantially spherical, or substantially semi-spherical, although other shapes are contemplated. As one skilled in the art can appreciate, the fixation element can comprise a pedicle screw, such as a standard fast-pitch, double-lead pedicle screw. As such, the head portion 110 can be configured to engage the particular insertion tool designed for the system 10. In one aspect, the head portion of the fixation element defines a screw tool bore 130 configured for engagement with the insertion tool. As illustrated in FIG. 9, the screw tool bore 130 can be a hex shaped bore or other shape that mates with a corresponding insertion tool or driver.

Figure 11:
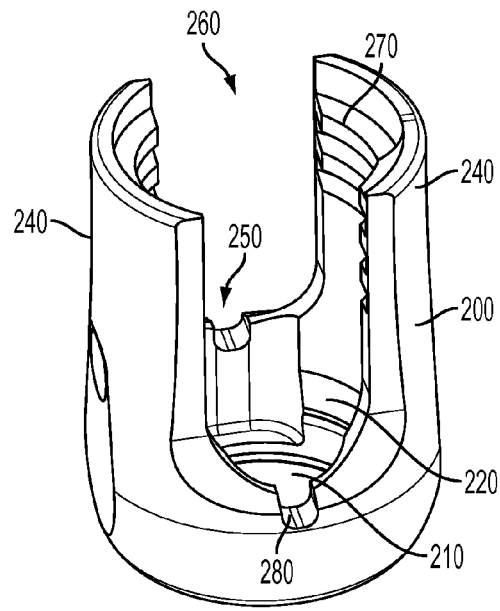
FIG. 11 is a perspective view of one aspect of a receiving element for use in a bone screw system.
Figure 12:
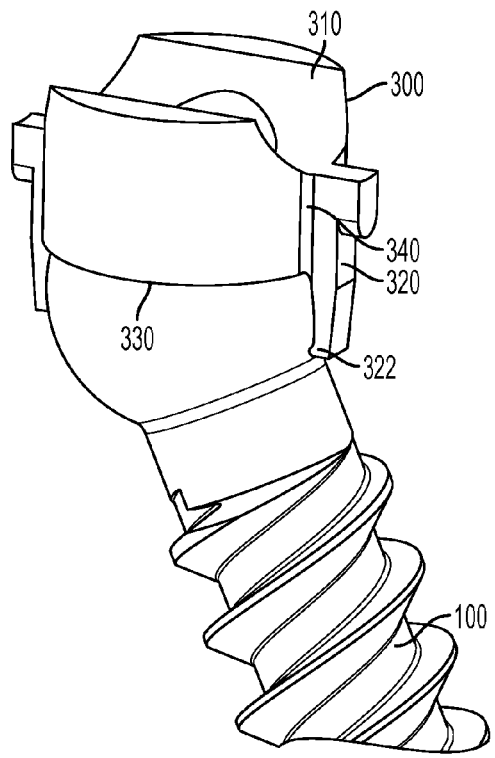
FIG. 12 is a perspective view of one aspect of a coupling element coupled thereto a head portion of a fixation element of for use with a bone screw system.
Figure 13:
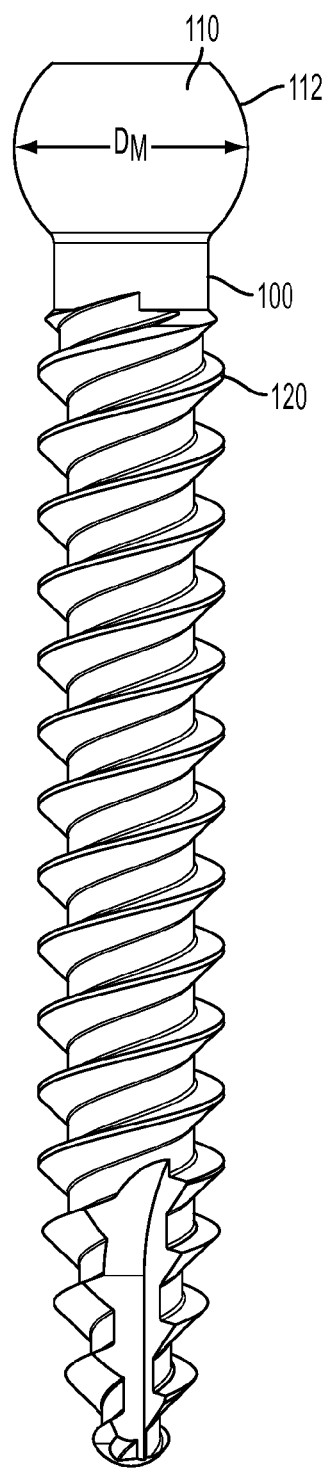
FIG. 13 is a side elevational view of one aspect of a fixation element for use with a bone screw system.
Figure 14:
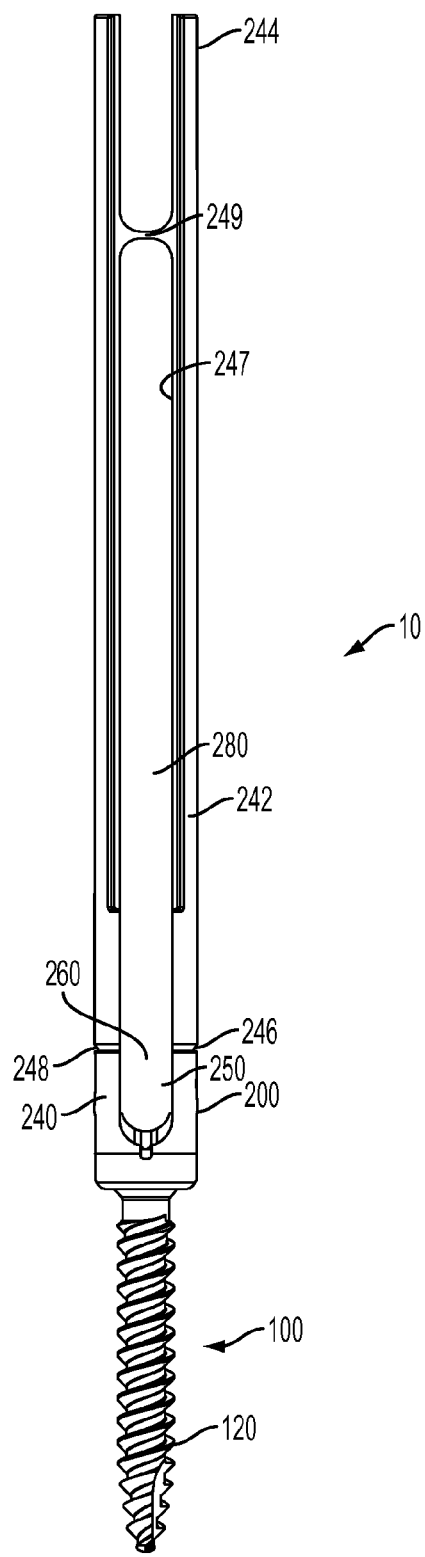
FIG. 14 is a front elevational view of one aspect of a bone screw system, showing a pair of leg extensions and a connector.
Figure 15:
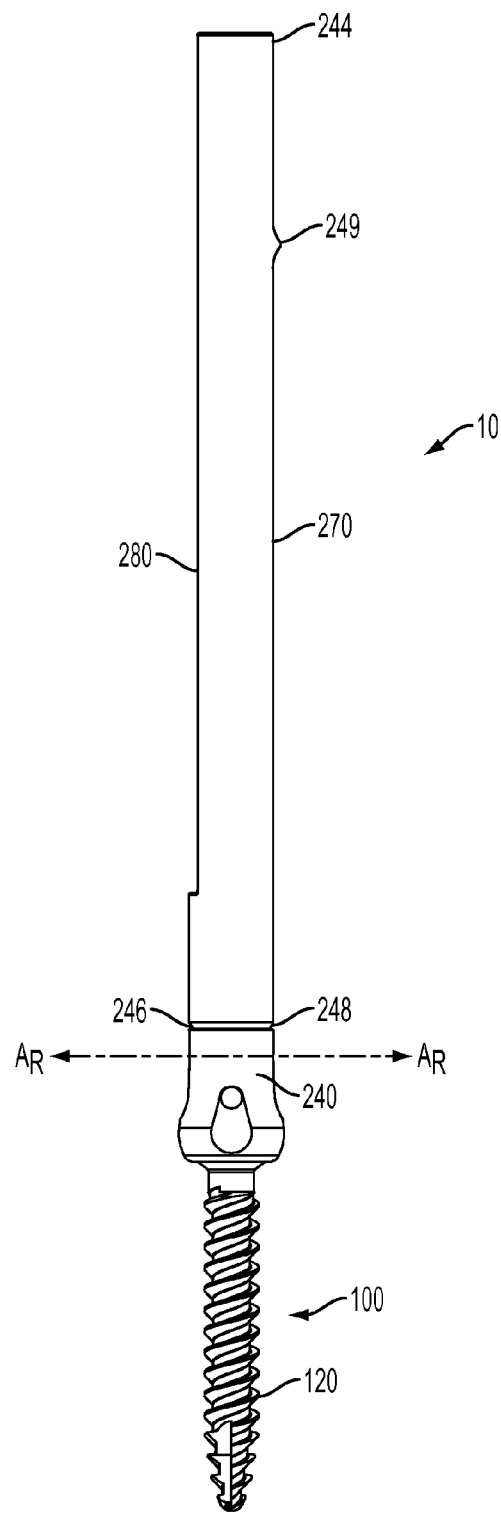
FIG. 15 is a side elevational view of the bone screw system of FIG. 14.
Figure 16:
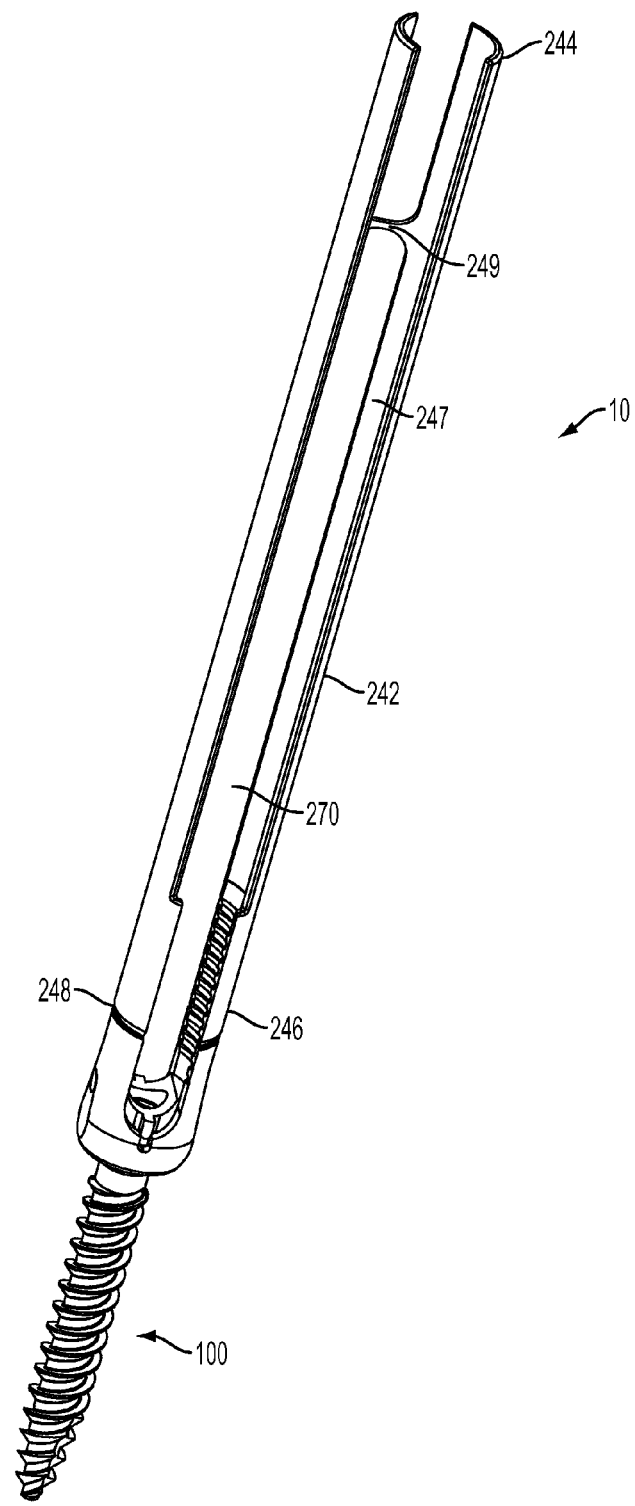
FIG. 16 is a perspective view of the bone screw system of FIG. 14.
Figure 17:
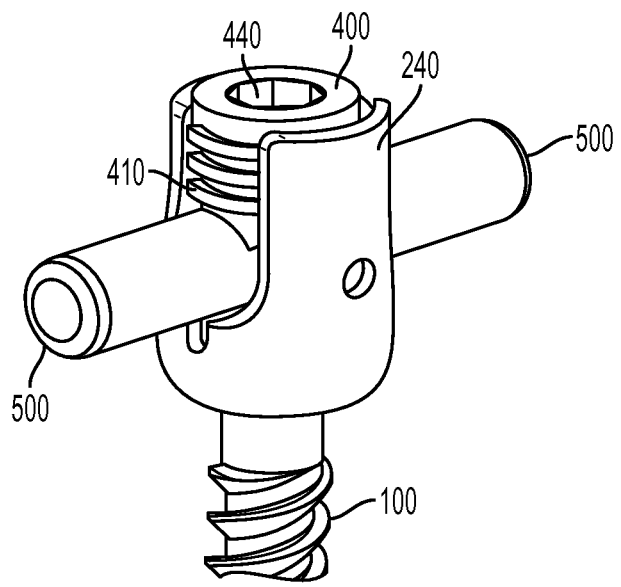
FIG. 17 is a perspective view of a bone screw system, showing a top saddle having a rod trough.
Figure 18A:
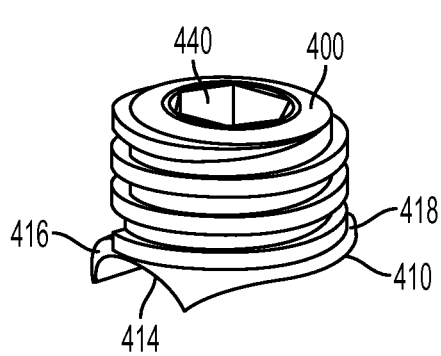
FIG. 18A is a perspective view of a compression element and a top saddle with a rod trough.
Figure 18B:
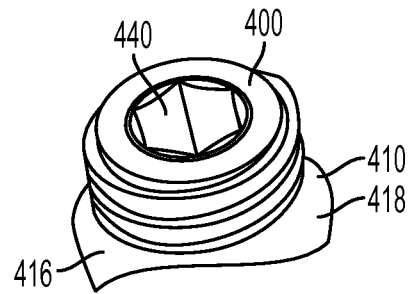
FIG. 18B is a perspective view of the compression element and top saddle of FIG. 18A.

The receiving element 200, as illustrated in FIG. 11, defines an internal bore 210 sized to receive the shank portion 120 of the fixation element 100 and a seat 220 adapted to support the head portion of the fixation element. The seat 220 of the receiving element is shaped to substantially conform to an exterior portion 112 of the head portion of the fixation element. The receiving element can be configured in various ways, as those skilled in the art can appreciate.

The receiving element is further adapted to receive a stabilizer rod 500. As such, in one aspect, the receiving element 200 comprises a pair of opposed legs 240 separated by a rod-receiving channel 250. As illustrated in FIG. 9, the rod 500 receiving channel 250 is sized for complementary engagement with a portion of the stabilizer rod. The compression element 400, as discussed below, is configured to work with the receiving element to compress the stabilizer rod onto the coupling element 300, although the system can work without the use of a coupling element. The compression of the stabilizer rod into the receiving element can be accomplished in several manners, including but not limited to, externally threading the two legs 240 for engagement with an internally threaded nut, or internally threading the two legs for engagement with an externally threaded set screw. As such, in this aspect, the pair of opposed legs 240 defines a compression element receiving chamber 260. In one exemplified aspect, the threads of the opposed legs and complimentary threads of compression element can comprise square threads. As one skilled in the art can appreciate, other thread patterns, such as but not limited to, inwardly tilted threads, dove tail threads, and the like, may be used.

In one exemplified aspect, the coupling element is positioned in the receiving element below the stabilizer rod when the stabilizer rod is in the receiving element. In one aspect, a top portion 310 of the coupling element is substantially saddle-shaped to substantially conform to the shape of the stabilizer rod to maximize contact surface area between the coupling element 300 and the stabilizer rod. The coupling element provides additional surface area of contact between the stabilizer rod and the head of the fixation element, so when the compression element is in place, the force of the compression element maintains the orientation of the fixation element.

The compression element is engagable with the receiving element 200, as discussed herein. In one aspect, the compression element 400 is adapted to move downward into the compression element receiving chamber 260 to translate a force to the stabilizer rod 500 and place it into contact with the coupling element, which translates a force onto the head portion of the fixation element and substantially fixes the position of the fixation element with respect to the receiving element. If the system is without a coupling element, the stabilizer rod can exert the force onto the head portion of the fixation element directly.

Figure 10:
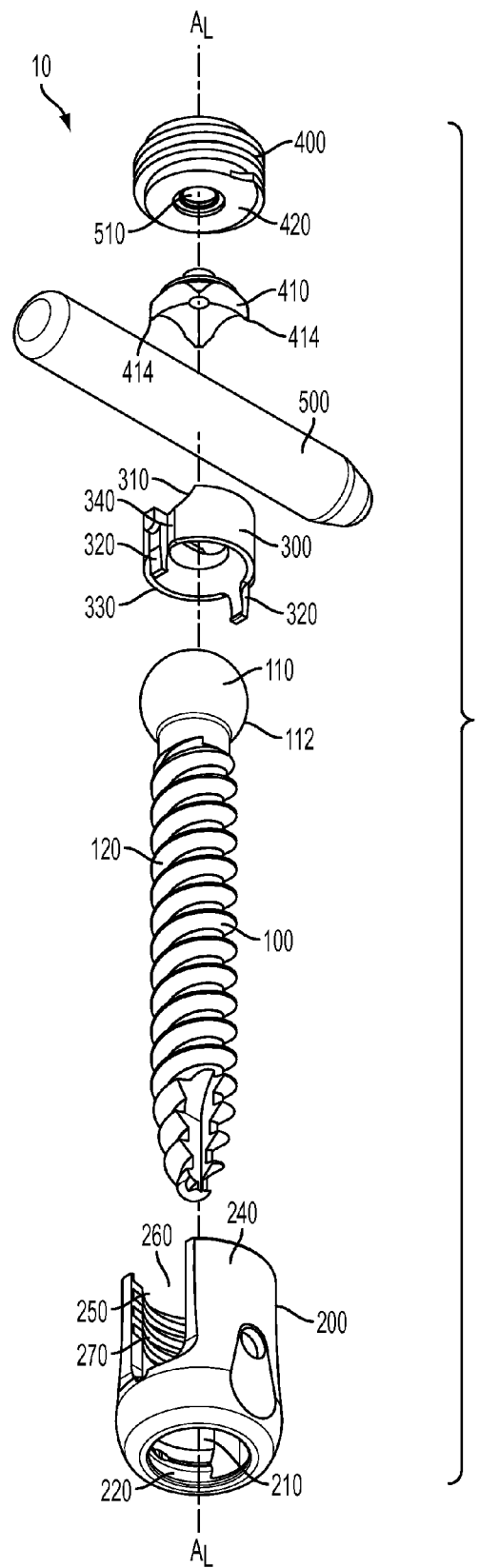
FIG. 10 is an exploded rear perspective view of the bone screw system of FIG. 1.

In still another aspect, the compression element can further comprise a top saddle 410 rotatingly positioned on its bottom face 420. It can, for example, be mounted to the bottom face 420 of the compression element. Alternately, as illustrated in FIG. 9, the top saddle 410 can comprise a male protrusion 412 designed to penetrate the compression element 400 and be retained thereby. In this aspect, the top saddle self-aligns into secure engagement with the stabilizer rod 500 as the top saddle moves downward toward the stabilizer rod. This design maximizes the contact surface area between the compression element 400 and the stabilizer rod. The top saddle 410 shown in FIG. 10 shows a top saddle 410 comprising a rod trough 414 substantially conformable to the surface of the stabilizer rod. In one exemplified aspect, the top saddle comprises a proximal end 416 and a distal end 418, where at least one of the two ends extends out of the compression element receiving chamber substantially along the longitudinal axis $A_R$ of the rod-receiving channel. In this fashion, the orientation of the top saddle is maintained to keep the rod trough 414 in substantially co-linear relation to the longitudinal axis of the rod-receiving channel and is prevented from rotating with the compression element by the two legs of the receiving element. In one aspect, the proximal end 416 extends further than the radius of the compression element receiving chamber. In another aspect, the distal end 418 extends further than the radius of the compression element receiving chamber. In yet another aspect, both ends extend further than the radius of the compression element receiving chamber.

The compression element 400 is designed to be driven into the compression element receiving chamber. In one aspect, the top face 430 of the compression element defines a set screw tool bore 440 configured for engagement with an insertion tool. The set screw tool bore 440 can be, but is not necessarily, configured to engage the same insertion tool as the screw tool bore discussed above.

Some practitioners may desire to position the bone screw system with the aid of one or more guide wires. In this case, the practitioner can place a guide wire into the desired target location. In this aspect, the system defines a coaxial aperture along the longitudinal axis $A_L$. Therefore, in this aspect, the compression element 400, the coupling element 300, and the fixation element each define a coaxial guide wire aperture 510. Where there is a top saddle present in the system, the top saddle also defines a coaxial guide wire aperture 510.

In another aspect, the bone screw system also comprises a pair of leg extensions 242. Each leg extension has a first end 244 and a second end 246, where the second end 246 is coupled to a respective opposed leg 240 of the receiving element 200. The pair of leg extensions define a first insertion tool pathway 270 therebetween one another and a second insertion tool pathway 280 therebetween one another.

In one aspect, the cross-sectional shape of the leg extensions are substantially similar to the cross-sectional shape of the leg to which it is coupled, each leg extension having the same outer cross sectional shape as the leg to which it is coupled. As can be appreciated, the cross-sectional dimensions of the leg extensions can also be substantially the same as the crosssectional dimensions of the legs to which they are coupled, although it is contemplated that the leg extensions can vary in shape and dimension from the legs to which they are coupled. The length of each leg extension can vary, but in any event, the first end of each of the leg extensions extends outside of the patient when the fixation element is positioned within the spine of the patient.

In an exemplified aspect, the two leg extensions are coupled to each respective leg at or near the leg extension's second end 246 in a manner such that the leg extension can be removed from the leg if desired. In one aspect, the leg and the leg extension can be integral, with a reduced thickness portion 248 at or near the point of coupling. In this aspect, sufficient radial pressure exerted near the reduced thickness portion will fracture the reduced thickness portion 248, thereby separating the leg extension from the leg. The reduced thickness portion can be interior, exterior, or both. Interior, in this instance, refers to the side of the leg extension or leg that faces the compression element receiving chamber.

The interior face 247 of each of the leg extensions need not be threaded like the legs of the receiving element. This configuration permits the compression element to slide between the leg extensions and into the compression element receiving chamber until it reaches the threaded portion. In one aspect, the interior face 247 of the leg extensions is threaded toward the second end 246.

Figure 19:
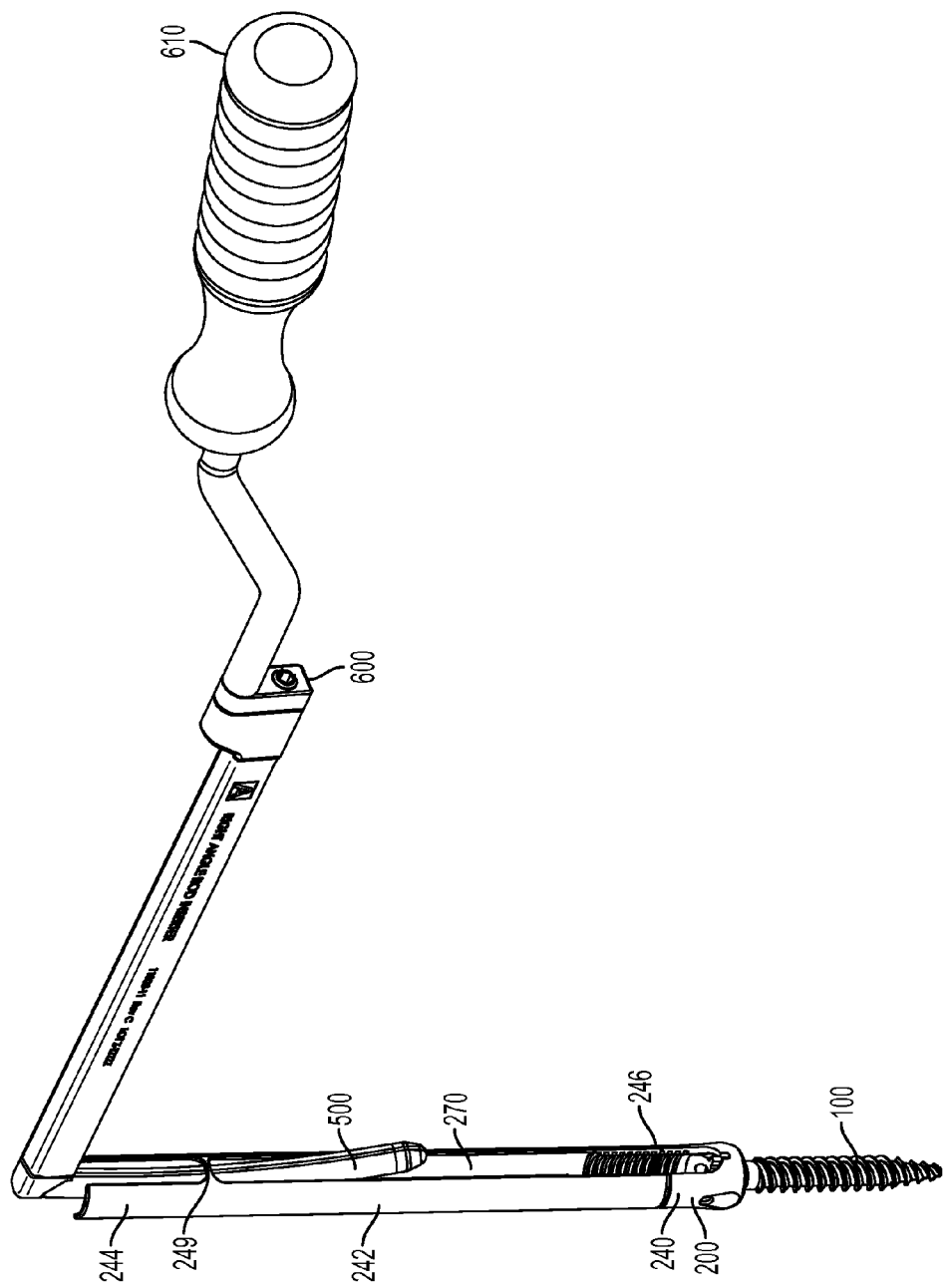
FIG. 19 is a perspective view of an insertion tool, inserting a stabilizer rod into a bone screw system with leg extensions.
Figure 20:
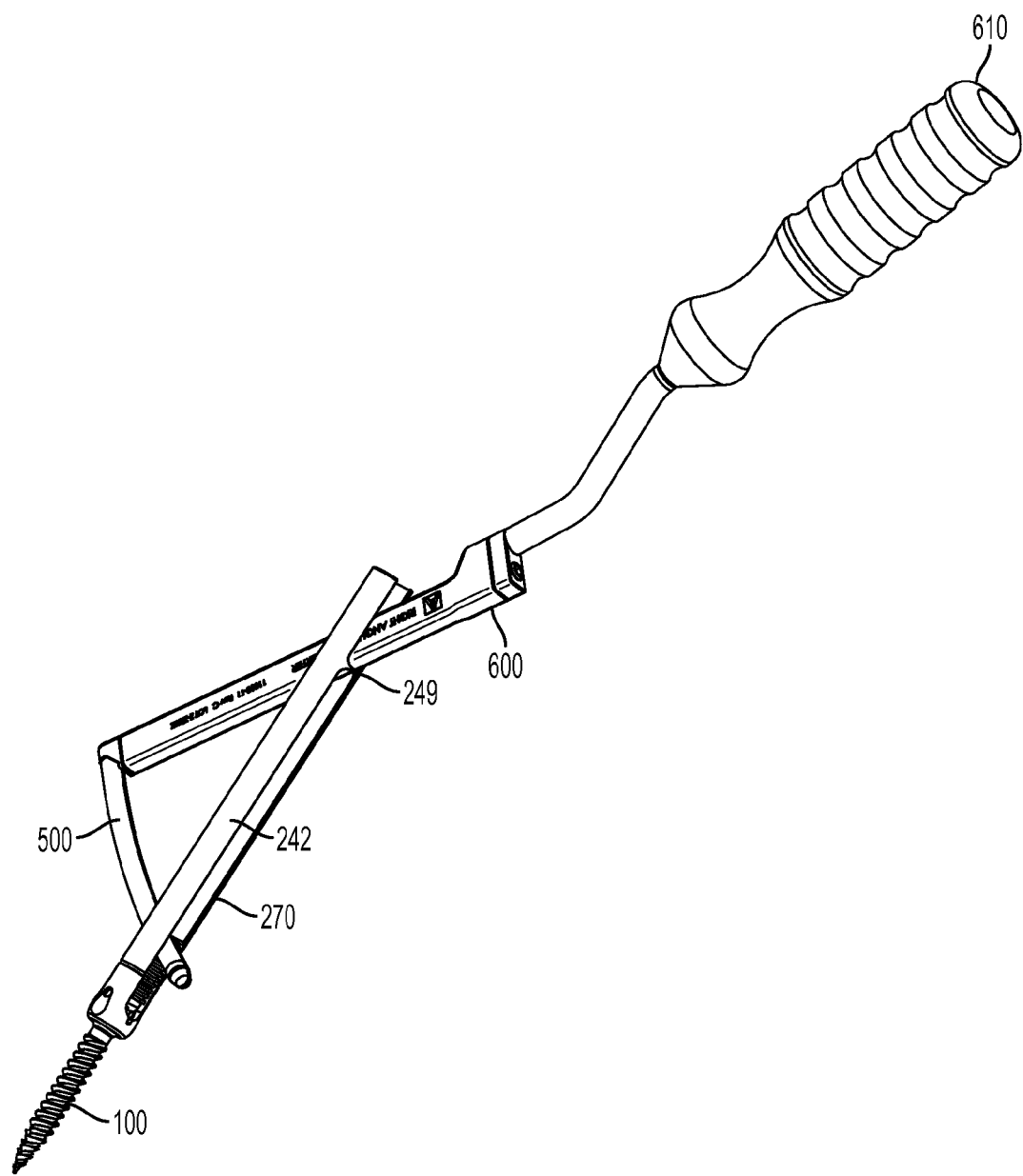
FIG. 20 is a perspective view of the insertion tool of FIG. 19, showing the insertion tool using the connector as a fulcrum to maneuver the stabilizer rod into position.
Figure 21:
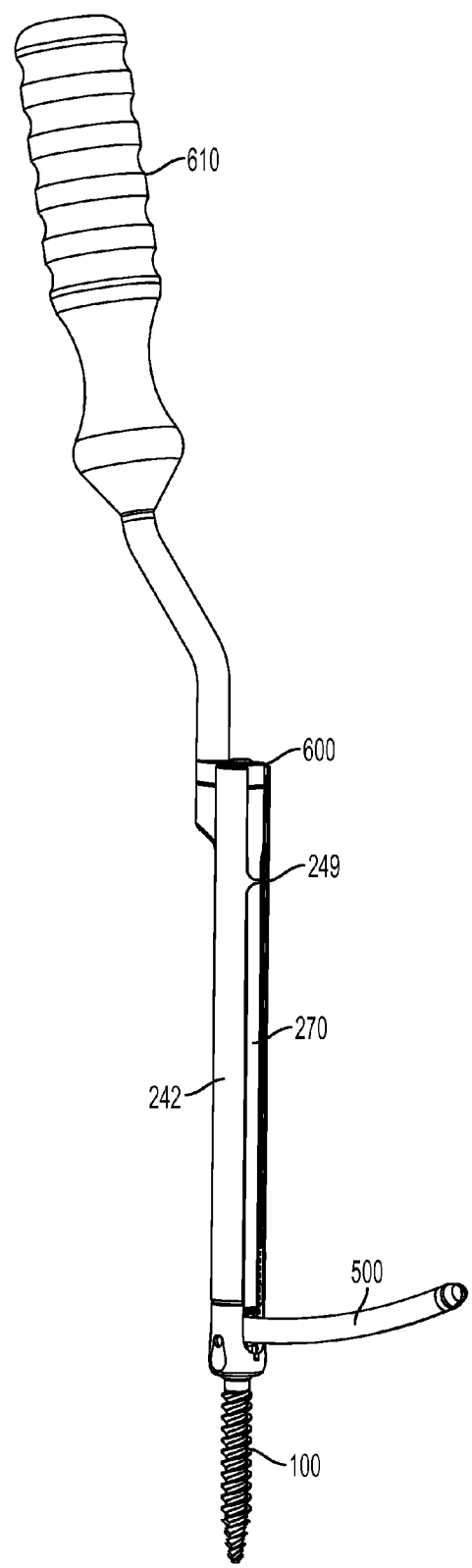
FIG. 21 is a perspective view of the insertion tool of FIG. 19, showing the insertion too using the connector as a fulcrum to further maneuver the stabilizer rod into position.

In another aspect, the two leg extensions are connected via a connector 249 positioned at a point spaced therefrom the first end of the leg extension and spanning the first insertion tool pathway 270. In one aspect, the connector is positioned substantially perpendicular to the longitudinal axis A.sub.L. Positioning the connector 249 a predetermined distance spaced from in near proximity to the first end provides a fulcrum point from which a rod insertion tool can rotate traversing both the first and second insertion tool pathways to allow the stabilizing rod and the insertion tool to pass to push a stabilizer rod into position within the receiving chamber, and wherein the second insertion tool pathway is open from the first end through the second end of the leg extensions to the rod receiving channel and wherein the leg extensions and the legs are integral, and wherein at a coupling point between the legs and leg extensions there is a reduced thickness. As seen in FIG. 19, the stabilizer rod is positioned between the leg extensions with the insertion tool. As the stabilizer rod is positioned lower and toward the second end of the leg extensions, the insertion tool is partially positioned between the leg extensions. At this point, the handle of the insertion tool can be lifted, using the connector as a fulcrum to push the stabilizer rod into position within the rod receiving channel.

As can be appreciated by one skilled in the art, the materials of construction can vary. The materials of construction are generally biocompatible materials for use in surgery. For example, the bone screw system 10 can comprise Titanium or a Titanium alloy, such as Ti 6-4 ELI. The system can also be bead blasted to increase frictional forces and to add stability to the system.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A bone screw system comprising:
an elongate fixation element adapted to engage a bone and having a head portion and a threaded shank portion;
a receiving element defining an internal bore sized to receive the shank portion of the fixation element and a seat adapted to support the head portion of the fixation element, the receiving element comprising a pair of opposed legs separated by a rod receiving channel sized for complimentary engagement with a stabilizer rod, wherein the pair of opposed legs defines a compression element receiving chamber;
a coupling element configured to be positioned in the receiving element below the stabilizer rod, the coupling element having a top portion having a saddle shape to conform to the shape of the stabilizer rod, the coupling element providing additional surface area of contact between the stabilizer rod and the head portion of the fixation element;
a compression element configured to engage a portion of the receiving element and be complimentarily received in the compression element receiving chamber, the compression element configured to compress the stabilizer rod into the receiving element to fix the position of the stabilizer rod with respect to the receiving element;
a pair of leg extensions, each leg extension having a first end and a second end, wherein the second end extends away from and is coupled to the respective opposed leg of the receiving element, each leg extension having the same outer cross sectional shape as the leg to which it is coupled, the pair of leg extensions thereby defining an extension of the compression element receiving chamber, wherein the pair of leg extensions define a first insertion tool pathway therebetween and a second insertion tool pathway therebetween on opposing sides of the extension of the receiving chamber, and wherein the pair of leg extensions is coupled by a connector spanning the first insertion tool pathway positioned at a point or predetermined distance spaced from and in near proximity to the first end to provide a fulcrum point against which an insertion tool holding the stabilizer rod can use the connector as a fulcrum from which the insertion tool can rotate traversing both the first and second insertion tool pathways to allow the stabilizing rod and the insertion tool to pass to push the stabilizer rod into position within the receiving chamber, and wherein the second insertion tool pathway is open from the first end through the second end of the leg extensions to the rod receiving channel and wherein the leg extensions and the legs are integral, and wherein at a coupling point between the legs and leg extensions there is a reduced thickness.

2. The bone screw system of claim 1, wherein the compression element is adapted to move downward into the compression element receiving chamber to force the stabilizer rod into contact with the coupling element and translate a force onto the head portion of the fixation element to substantially fix the position of the fixation element with respect to the receiving element.

3. The bone screw system of claim 1, wherein the compression element comprises external threads and an interior portion of the opposed legs comprises internal threads complimentary to the external threads.

4. The bone screw system of claim 3, wherein an interior portion of the leg extensions each have internal threads.

5. The bone screw system of claim 1, wherein the compression element, the coupling element and the fixation element each define a coaxial guide wire aperture.

6. The bone screw system of claim 1, wherein the leg extensions have a cross sectional shape and the opposed legs each have a cross-sectional shape, and wherein the cross-sectional shape of the leg extensions is substantially similar to the cross-sectional shape of the opposed legs.

7. The bone screw system of claim 1, wherein the leg extensions are removably coupled to the respective legs at the coupling point.

* * * * *